United States Patent
Lueerssen et al.

(10) Patent No.: US 7,429,735 B2
(45) Date of Patent: Sep. 30, 2008

(54) HIGH PERFORMANCE CCD-BASED THERMOREFLECTANCE IMAGING USING STOCHASTIC RESONANCE

(75) Inventors: Dietrich Lueerssen, Kidlington (GB); Rajeev J. Ram, Arlington, MA (US); Janice A. Hudgings, South Hadley, MA (US); Peter M. Mayer, Cambridge, MA (US)

(73) Assignees: Mass Institute of Technology (MIT), Cambridge, MA (US); Mount Holyoke College, South Hadley, MA (US)

( * ) Notice: Subject to any disclaimer, the term of this patent is extended or adjusted under 35 U.S.C. 154(b) by 25 days.

(21) Appl. No.: 11/376,722

(22) Filed: Mar. 15, 2006

(65) Prior Publication Data

US 2006/0274151 A1 Dec. 7, 2006

Related U.S. Application Data

(60) Provisional application No. 60/661,832, filed on Mar. 15, 2005.

(51) Int. Cl.
*G01N 21/17* (2006.01)
(52) U.S. Cl. ............... 250/341.8; 374/130; 356/447
(58) Field of Classification Search ............... 250/341.8; 374/130; 356/447
See application file for complete search history.

(56) References Cited

U.S. PATENT DOCUMENTS

| 5,223,932 A | 6/1993 | Thomas et al. |
| 5,286,968 A | 2/1994 | Fournier et al. |
| 5,440,338 A | 8/1995 | Roundy et al. |
| 6,028,543 A * | 2/2000 | Gedcke et al. ............... 341/131 |
| 2002/0126732 A1 | 9/2002 | Shakouri et al. |
| 2003/0126732 A1 | 7/2003 | Okada |

FOREIGN PATENT DOCUMENTS

WO WO03052366 11/2003

OTHER PUBLICATIONS

Christofferson, et al., "Thermoreflectance Imaging of Superlattice Micro Refrigerators," SEMITHERM XVII symposium proceedings, San Jose, CA, Mar. 2001.
Thorne, et al., "High-resolution thermoreflectance miscroscopy," *Mat. Res. Soc. Symp. Proc.* vol. 738 2003 Materials Research Society G12.9.1-G12.9.6.

(Continued)

*Primary Examiner*—David P. Porta
*Assistant Examiner*—Jessica L Eley
(74) *Attorney, Agent, or Firm*—Thomas J. Engellenner; Reza Mollaaghababa; Nutter McClennen & Fish LLP

(57) ABSTRACT

The invention is directed to systems and methods of digital signal processing and in particular to systems and methods for measurements of thermoreflectance signals, even when they are smaller than the code width of a digital detector used for detection. For example, in some embodiments, the number of measurements done is selected to be sufficiently large so as to obtain an uncertainty less than the code width of the detector. This allows for obtaining images having an enhanced temperature resolution. The invention is also directed to methods for predicting the uncertainty in measurement of the signal based on one or more noise variables associated with the detection process and the number of measurement iterations.

32 Claims, 11 Drawing Sheets

OTHER PUBLICATIONS

Christenson, et al., "FLIM Sheds Light on DNA," *Spie Magazine of Photonics Technologies and Applications* Jan. 2004.

Gammaitoni, Stochastic resonance and the dithering effect in threshold physical systems, vol. 52—The American Physical Society, pp. 4691-4698, Nov. 1995.

Matatagui, et al., "Theremoreflectance in Semiconductors," *Physical Review* vol. 176, No. 3, pp. 950-960, Dec. 15, 1968.

Grauby, et al. "High resolution photothermal imaging of high frequency phenomena using a visible charge coupled device camera associated with a multichannel lock-in scheme" *Review of Scientific Instruments, American Institute of Physics, US vol. 70* (1999).

Luerssen, D et al., "Nanoscale thermoreflectance with 10mk temperature resolution using stochastic resonance" *Semiconductor Thermal Measurement and Management Symposium, 2005 IEEE*, San Jose, CA (Mar. 2005).

* cited by examiner

INPUT CURRENT AT FREQUENCY = $f_0$

TEMPERATURE OSCILLATES AT FREQUENCY = $2f_0$

DOTTED LINES SHOW CAMERA TRIGGER POINTS AT FREQUENCY = $8f_0$ $\Delta R/R = 1.51 \times 10^{-3}$
$c = 3387$ $\Delta R/R = 3.92 \times 10^{-4}$
$c = 1527$

HIGH PERFORMANCE CCD-BASED THERMOREFLECTANCE IMAGING USING STOCHASTIC RESONANCE

RELATED APPLICATIONS

This application claims priority to a provisional application entitled "High Performance CCD-based Thermoreflectance Imaging Using Stochastic Resonance" having a Ser. No. 60/661,832, which was filed on Mar. 15, 2005 and is herein incorporated by reference.

FEDERALLY SPONSORED RESEARCH

The invention was made with Government Support under Grant Number ESC-0321449, awarded by NSF. The Government has certain rights in the invention.

BACKGROUND

The present invention relates generally to systems and methods for digital signal processing, and in particular to systems and methods that are suitable for performing thermoreflectance measurements with enhanced spatial and temperature resolutions.

Themoreflectance is a well-established non-contact method for measuring temperature distributions on a variety of different sample types. In the past decade, thermal imaging (as opposed to single point measurements) has become increasingly popular. As a result, different ways to achieve this goal have been published. There is a consensus in the recent literature (as recent as January 2005) that the quantization limit of an n-bit CCD, typically utilized for detecting reflected photons in thermoreflectance measurements, limits the detectable change in the reflectivity, and therefore seemingly limits the temperature resolution of the measurements.

In many thermoreflectance measurement systems, as well as in a variety of other systems, analog to digital conversion (ADC) is employed to convert an analog signal (i.e., allowing floating point results) into a digital one (i.e., only using integer numbers). The smallest digital unit is known as the least significant bit (LSB), or, in the language of signal conversion, the code. The code, when combined with the analog-digital conversion factor, yields the smallest detectable (analog) signal change, also called the code width. It is well established that for single channel ADC, a method known as "oversampling and averaging" can increase the effective number of bits of the ADC. Devices based on this principle are commonly known as "ΣΔ ADC", "sigma delta ADC" or a similar nomenclature.

Conventional thermoreflectance systems and methods, however, suffer from a number of shortcomings. For example, the spatial resolution achieved by conventional infrared imagers operating based on black-body emission is typically limited to ~5 microns while the temperature resolution of such systems is in a range of few hundred mK to 1K.

Hence there exists a need for enhanced methods and systems of digital signal processing. There is also a need for such methods and systems that allow performing thermoreflectance measurements with improved spatial and temperature resolution.

SUMMARY

In one aspect, the present invention provides a thermoreflectance apparatus that can combine a high spatial resolution, for example, a resolution in a range of about 200 nanometers to about 1 micron (e.g., 250 nm), with high temperature resolution. For example, the temperature resolution can be in a range of about 1 milliKelvin (mK) to about 1 K (one Kelvin), and preferably better than about 10 mK, e.g., in a range of about 1 mK to about 10 mK. By way of example, such enhanced temperature resolutions can be achieved in a thermoreflectance system according to the teachings of the invention by modulating the sample's temperature and iterating signal acquisition over a much larger number of periods than utilized in conventional thermoreflectance techniques. Moreover, it has been discovered that "noise induced threshold crossing" (also known as "stochastic resonance") can be utilized in a multi-threshold imaging system, such as ADC or CCD, to detect signals smaller that the code width associated with the imaging system. For example, in some embodiments, in each period of the temperature modulation, four reflectance images can be acquired, and the acquisition of such images can be repeated for about $10^3$ to about $2 \times 10^6$ periods of the temperature modulation to obtain a temperature resolution of about 10 mK or better (the total number of acquired images is then in a range of about $4 \times 10^3$ to about $8 \times 10^6$). In this manner, the effective number of bits of a digital detector (e.g., a CCD) utilized for detecting photons from an illuminated sample can be increased.

In a related aspect, the invention provides a method of performing thermoreflectance measurements that includes utilizing a digital imaging system to detect a number of images of radiation reflected from a surface of a sample in response to an illuminating radiation while applying a temperature modulation to the sample. For example, a map of relative change in reflectivity of the sample surface can then be derived based on the acquired images. The number of the acquired images is selected to be sufficiently large, e.g., on the order of $10^6$, to ensure that the signal-to-noise ratio of the measured reflectivity signal is within a pre-determined limit appropriate to the specific application. Preferably, the number of iterations ranges from about $10^3$ to about $10^8$, and more preferably from about $10^4$ to about $10^7$. While in some embodiments, four images are acquired per iteration, in other embodiments, a different number of images per iteration can be obtained.

In a related aspect, in the above method of performing thermoreflectance measurements, a digital lock-in technique is employed for acquiring the images. By way of example, a digital lock-in technique commonly known as the four-bucket lock-in technique can be utilized to acquire the images.

In another aspect, a method of performing thermoreflectance measurements is disclosed that includes modulating the temperature of a sample at a selected modulation frequency (f) while illuminating a portion of the sample with radiation having one or more selected wavelength components (e.g., wavelength of a few hundred nanometers). A digital imaging system having a plurality of pixels is utilized to detect radiation reflected from the sample in response to the illumination in order to generate reflectance images of the sample. The imaging system is triggered to obtain a selected number of reflectance images in one period of the temperature modulation. A map of relative change in reflectivity of the sample can be calculated from the images and the step of acquiring the reflectance images can be iterated over a sufficient number of periods of the temperature modulation so as to obtain an uncertainty in the calculated relative reflectivity such that signals smaller than a code width of the digital imaging system can be detected.

In a related aspect, in the above method, the uncertainty in the calculated relative change in reflectance per pixel can be less than about $10^{-5}$, $10^{-6}$ and preferably less than about $10^{-7}$.

In another aspect, the iterating step in the above method is performed over least about $10^3$ periods of the temperature modulation, or over at least about $10^4$, $10^5$, or $10^6$ periods of the temperature modulation.

In a related aspect, the above method of performing thermoreflectance measurements calls for obtaining four reflectance images within each period of the temperature modulation. The respective images in a plurality of modulation periods can be summed to obtain a signal $I_k$ in accordance with the following relation:

$$I_k(x, y) \equiv \sum_{i=1}^{N} \left[ \left( \frac{4}{T} \int_{(4i+k)\frac{T}{4}}^{(4i+k+1)\frac{T}{4}} [c(x, y) + \Delta(x, y) \cos(\omega t + \Phi(x, y) + \Psi)] dt \right) + d(x, y) \right]$$

$$k \in \{1, 2, 3, 4\}$$

In this equation c represents the time independent component of the signal, $\Delta$ is the amplitude of the modulated component of the signal, d is the noise present prior to quantization, $\Delta R/R$ is the intensity of the thermoreflectance signal, $\phi$ represents the phase of the temperature modulation, N is the number of iterations, $\omega$ is frequency of modulation, T is the period of modulation and $\Psi$ is an arbitrary uniform phase offset.

In another aspect, the number of iterations N is selected to be sufficiently large such that the smallest measurable thermoreflectance signal ($\Delta R/R$) can be less than a code width of a digital detector utilized to acquire the images.

In a related aspect, in the above method of performing thermoreflectance measurements, a map of relative temperature change of the sample is calculated based on the measured relative reflectance-change map. The relative temperature modulation map can exhibit a temperature resolution in a range of about 1 mK to about 1 K, or more preferably in range of about 1 mK to about 10 mK. Further, the temperature modulation map can exhibit a spatial resolution in a range of about 200 nanometers to about 1 micron, or in a range of about 200 nm to about 500 nm, or more preferably in a range of about 200 nm to about 300 nm.

In other aspects, the present invention provides methods for predicting the uncertainty in the measurements of a modulated signal based on the number of measurement iterations and selected characteristics of the measurement system. By way of example, in one aspect, a method of digital signal processing is disclosed that includes determining one or more variables indicative of the noise characteristics associated with detecting a modulated radiation signal by a digital detector, and estimating the signal-to-noise ratio of an average of a plurality of output signals to be generated by the detector in response to the modulated signal as a function of the noise variables and the number of the output signals.

In a related aspect, the noise variables can be determined by measuring output signals of the detector in absence of the radiation.

In another aspect, the invention provides a method of digital signal processing that includes determining one or more variables indicative of the noise characteristics of a digital detector employed to detect a radiation signal modulated about a substantially constant level, and predicting the signal-to-noise ratio of a plurality of read-out signals to be generated by the detector in response to the detection of the modulated signal as a function of (i) the values of the noise variables, (ii) an average detector read-out signal over a measurement period and (iii) the number of the read-out signals.

In another aspect, a method of digitally detecting a modulated signal is disclosed. The method calls for triggering a digital detector, for each of a plurality of modulation periods of the signal, at a plurality of time intervals to generate a plurality of read-out signals in response to detection of the modulated signal. A plurality of average output signals are generated, each of which corresponds to an average of the read-out signals obtained at similar time intervals in the modulation periods. This is followed by deriving the magnitude of the modulated signal (e.g., an amplitude of the modulated component) based on the average output signals. The number of the read-out signals is selected to be sufficiently large such that an uncertainty in the derived magnitude of the modulated signal is less than a code width of the detector.

In a related aspect, the modulated signals can correspond to any of thermoreflectance, electroreflectance, photoreflectance, or piezoreflectance of a substrate.

In another aspect, a method of estimating the signal-to-noise ratio of a signal is disclosed that utilizes the uncertainty in the measured phase of a modulating signal (that is, the phase noise) to predict the signal-to-noise ratio of the signal's amplitude. For example, in a thermoreflectance measurement, the phase uncertainty calculated based on the phase information obtained from reflectance signals detected by a number of neighboring pixels (e.g., a 5×5 pixel area) can be utilized to derive the phase uncertainty, which in turn can predict the signal-to-noise ratio of the relative reflectivity. The phase uncertainty can be utilized to set a threshold at which the iteration of data acquisition can be terminated. That is, the phase uncertainty can be employed as an indicator identifying when a selected signal-to-noise of the relative reflectivity has been achieved, as described in more detail below. In one preferred embodiment, the experimental uncertainty in phase measurements of neighboring pixels is measured over an area ranging from 9 pixels (3×3) to 49 pixels (7×7).

In yet another aspect, a method of performing thermoreflectance measurements is disclosed in which the temperature of a sample can be modulated at a selected modulation frequency $f_1$, while illuminating a portion of the said sample with radiation modulated at a different frequency $f_2$. A digital imaging system detects the radiation reflected from the sample and modulated at a difference frequency equal to a difference of said $f_1$ and $f_2$ frequencies. This allows reflectance images of the sample to be generated. The digital imaging system is triggered to obtain a selected number of reflectance images in one cycle of the oscillation of intermediate frequency. A map of the relative reflectance changes of said sample can then be calculated from the reflectance images. Iterating the step of acquiring reflectance images over a sufficient number of oscillation cycles of the intermediate frequency, allows calculating the relative reflectance changes with sufficiently small uncertainty. This allows detection of signals smaller than the code width of said digital imaging system.

In another aspect, the above mentioned method eliminates the need for additional and independent experiments. Thus, precious experimental time and effort can be saved. In addition, the method of the present invention can be used to stop an experimental run once a pre-determined signal-to-noise ratio has been achieved. More specifically, the method allows the determination of the signal-to-noise ratio from the measurement itself, with no need for prior knowledge of the signal magnitude and without recourse to multiple or independent measurements. The applicability of this method is not limited to the thermoreflectance technique described herein by way of example, but is more generally applicable to a variety of other imaging techniques. For example, it can be employed to process signals obtained with other imaging methods that employ the 4bucket digital lock-in technique, such as lock-in infrared imaging. More generally, this method can be characterized as a method of signal processing in which a temporally modulated signal is detected at a plurality of time intervals to generate a set of discrete data points corresponding to that signal. The data can be utilized to derive the amplitude of the signal, along with its phase as well as an uncertainty associated with the derived phase. The signal-to-noise ratio of the signal's amplitude can be calculated based on the phase uncertainty.

In another aspect, the present invention provides a method of signal processing, by detecting a temporally modulated signal at a plurality of time intervals. In one aspect this method allows generating a set of discrete data points corresponding to said signal, and utilizing the data to derive the amplitude and phase of said signal. More specifically, this method allows deriving the uncertainty associated with phase of said signal, and allows the estimation of the signal-to-noise ratio of said derived amplitude based on said phase uncertainty.

In still another aspect, the present invention provides a method of data acquisition that includes collecting a set of data points corresponding to a temporally modulated signal. In one aspect, the invention of the present application allows deriving the phase and phase uncertainty associated with the signal form the data acquired. More specifically, this method allows for the iteration of the above steps until the phase uncertainty reaches a pre-selected threshold.

Thus, in one aspect, the present invention provides a thermoreflectance apparatus and methods that combine a high spatial resolution (e.g., 250 nm) with a good temperature resolution, e.g., in a range of about 1 mK to about 1 K, and preferably in a range of about 1 mK to about 10 mK. This combination opens the door to new applications, such as the measurement of the optical power distribution in photonic devices as an important characterization technique for photonic integrated circuits. In addition, the teachings of the invention can be utilized as an important quality control tool, for example in the thermal profiling of vertical cavity surface emitting lasers.

DETAILED DESCRIPTION

The teachings of the present invention relate generally to processing of digital signals, and particularly to methods of digital signal processing that employ digital lock-in techniques. In many embodiments, the teachings of the invention can be used to analyze signals with an associated uncertainty that is less than the code width of a digital detector utilized to detect the signal. Although in the following embodiments various aspects of the invention are described in connection with thermoreflectance imaging, it should be realized that the teachings of the invention can be applied equally to other measurement techniques such as electroreflectance or piezoreflectance to generate high resolution images.

Figure 1A:
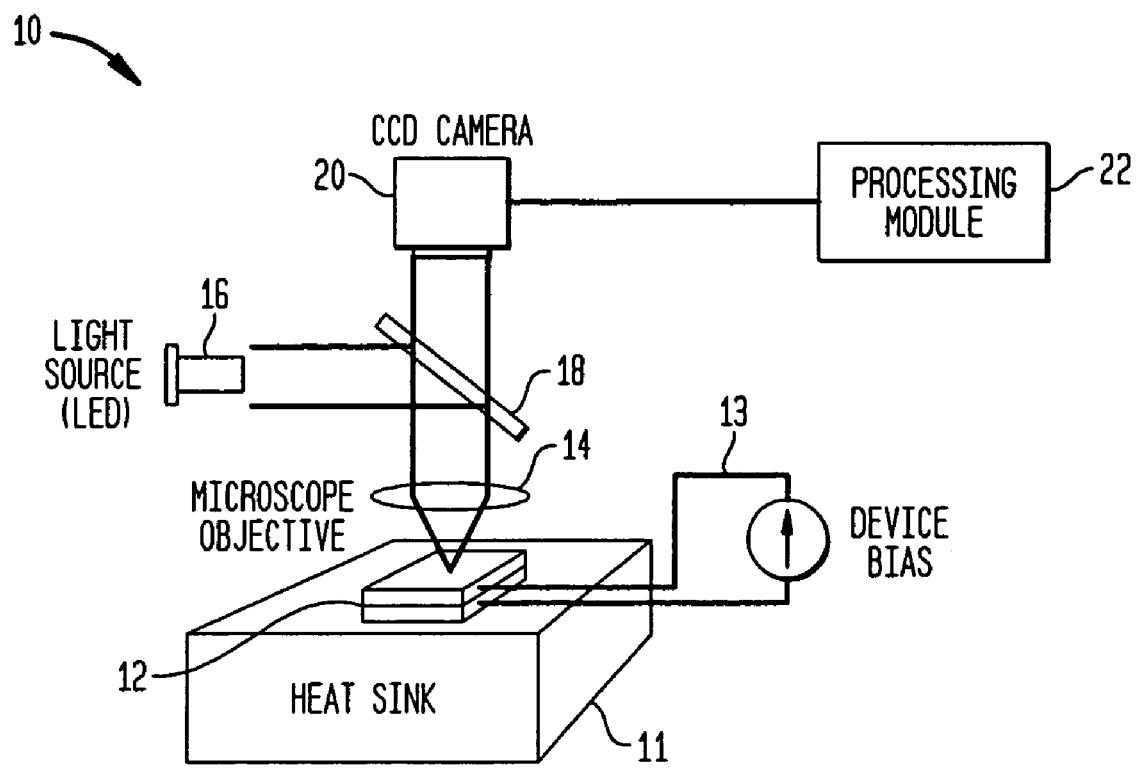
FIG. 1A is a schematic diagram of a thermoreflectance apparatus in accordance with an embodiment of the present invention.

FIG. 1A schematically illustrates an apparatus 10 according to one exemplary embodiment of the invention for measuring thermoreflectance of a sample 12 (for example, a semiconductor device), which is mounted on a heat sink 11. A microscope 14 focuses light, generated by a light source such as a light emitting diode (LED) 16 and directed to the microscope via a beam splitter 18, onto the sample, and a CCD camera 20 detects the light reflected from the sample. The sample is temperature-modulated in a manner known in the art (periodically heated and cooled by employing, e.g., an electrical current applied to the sample via a current source 13, modulated laser beams absorbed by the sample, or via temperature changes of the sample mount) at a selected modulation frequency (f), and a multi-channel lock-in technique is utilized to detect the reflected light by the CCD camera. As discussed in more detail below, in this embodiment, the camera is triggered at a frequency that is four times the temperature modulation frequency to acquire four images within a period (T) of the sample modulation. The data collected by the CCD camera can be transferred to a processing module 22 for analysis as described in more detail below.

The camera used in this exemplary embodiment is a 12 bit grayscale CCD, which can deliver up to 60 frames per second through a USB2.0 bus, and has 652 by 494 pixels. It should, however, be understood that other digital detectors and camera types can also be employed. More particularly, the teachings of the invention are not limited to the specific camera, communications bus, or other exemplary parameters (e.g., frames/second, number of pixels) employed in this illustrative embodiment.

Pipelining allows the collection of individually externally triggered images while maintaining a high duty cycle of typically more than 98%. A digital lock-in method, commonly referred to as four-bucket method is employed, where four images per period "T" of the sample modulation are acquired and summed pixel by pixel. After data acquisition is complete, the processing module 22 reconstructs the magnitude and phase of the reflected signal from the four distinct phase bins using an analysis similar to that of the four-point discrete Fourier Transform.

The "four-bucket" lock-in technique provides at least two advantages: (1) it allows for an economical way to obtain modulated images, since only four images (one for each phase bin) need to be kept in memory throughout the procedure, and (2) it allows one to overcome, if applicable, relatively slow readout speed of the CCD-array.

Figure 2A:
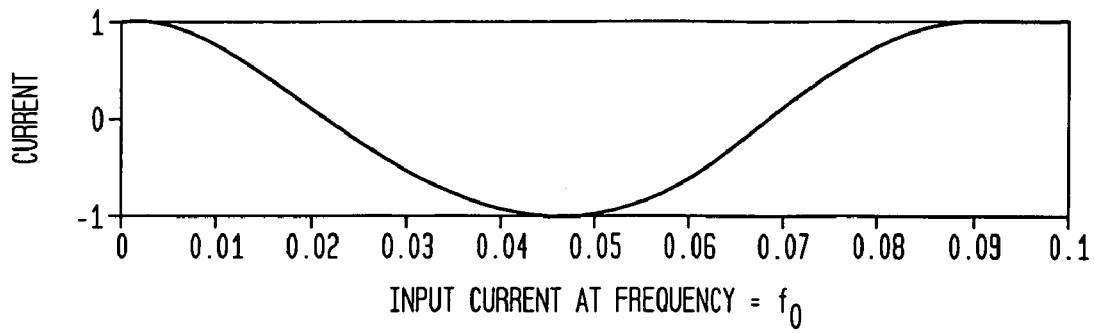
FIG. 2A depicts an exemplary input current applied to a substrate under study at a frequency f.
Figure 2B:
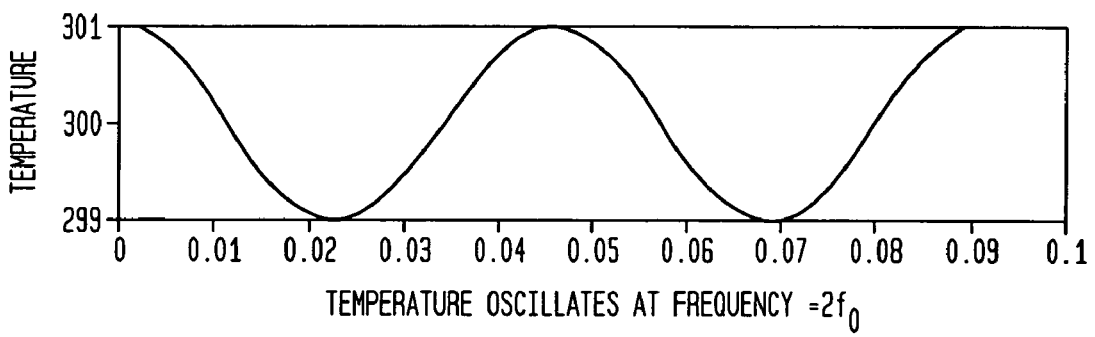
FIG. 2B shows that the temperature of the substrate to which the input current of FIG. 2A is applied oscillates at a frequency twice that of the input current.
Figure 2C:
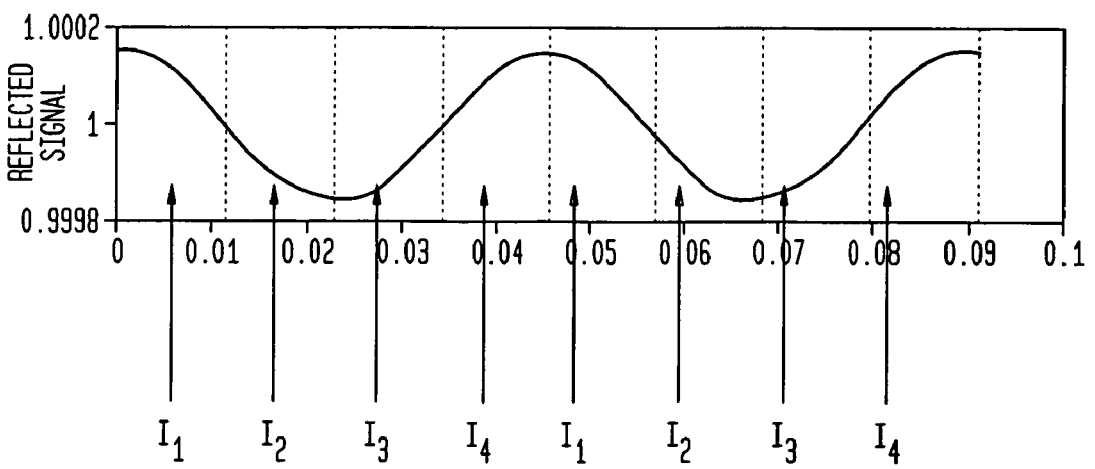
FIG. 2C shows acquiring images of a substrate to which the temperature modulation of FIG. 2B is applied four times within each modulation period.

By way of further illustration, the use of the four-bucket method in connection with a thermoreflectance measurement performed by the above exemplary apparatus 10 is schematically depicted in FIGS. 2A-2C. Ohmic heating of a sample under study can occur via an input current supplied at a frequency 'f'. The sample's temperature oscillates at a frequency '2f', and a digital detector is triggered to image the reflected light at a frequency '8f'. In each temperature modulation period, four images of the sample are acquired. As discussed in more detail below, the acquisition of the images is repeated over sufficient number of modulation periods to ensure that the uncertainty in signal amplitude, derived as an average of the signals obtained over the modulation periods, is less than the code width of the CCD camera. Although in this embodiment, four images are acquired per temperature modulation cycle, in other embodiments, a different number of images can be obtained per modulation cycle.

The four images ($I_k$, k=1 ... 4), which stem from the time integration of the signal with subsequent truncation of sub-threshold signal contributions, can be represented mathematically as follows:

$$I_k(x, y) \equiv \sum_{i=1}^{N} \left[ \left( \frac{4}{T} \int_{(4i+k)\frac{T}{4}}^{(4i+k+1)\frac{T}{4}} [c(x, y) + \Delta(x, y) \cos(\omega t + \Phi(x, y) + \Psi)] dt \right) + d(x, y) \right] \quad (1)$$

$$k \in \{1, 2, 3, 4\}$$

In this equation, 'c' represents the time independent signal (dc-part of reflected light), 'Δ' denotes its modulation, 'd' is the noise present prior to quantization, ΔR/R is the intensity of the thermoreflectance signal and φ represents the phase of the harmonic heating. The relative magnitude and phase of the thermoreflectance signal can be recovered using the following equations (2) and (3):

$$\left|\frac{\Delta R}{R}\right|_{ideal} = \frac{\pi}{\sqrt{2}} \frac{\sqrt{(I_1 - I_3)^2 + (I_2 - I_4)^2}}{I_1 + I_2 + I_3 + I_4} = \frac{\Delta}{c} \quad (2)$$

$$\Phi_{ideal} = \arctan\left(\frac{I_1 - I_2 - I_3 + I_4}{I_1 + I_2 - I_3 - I_4}\right) - \Psi = \Phi \quad (3)$$

Figure 1B:
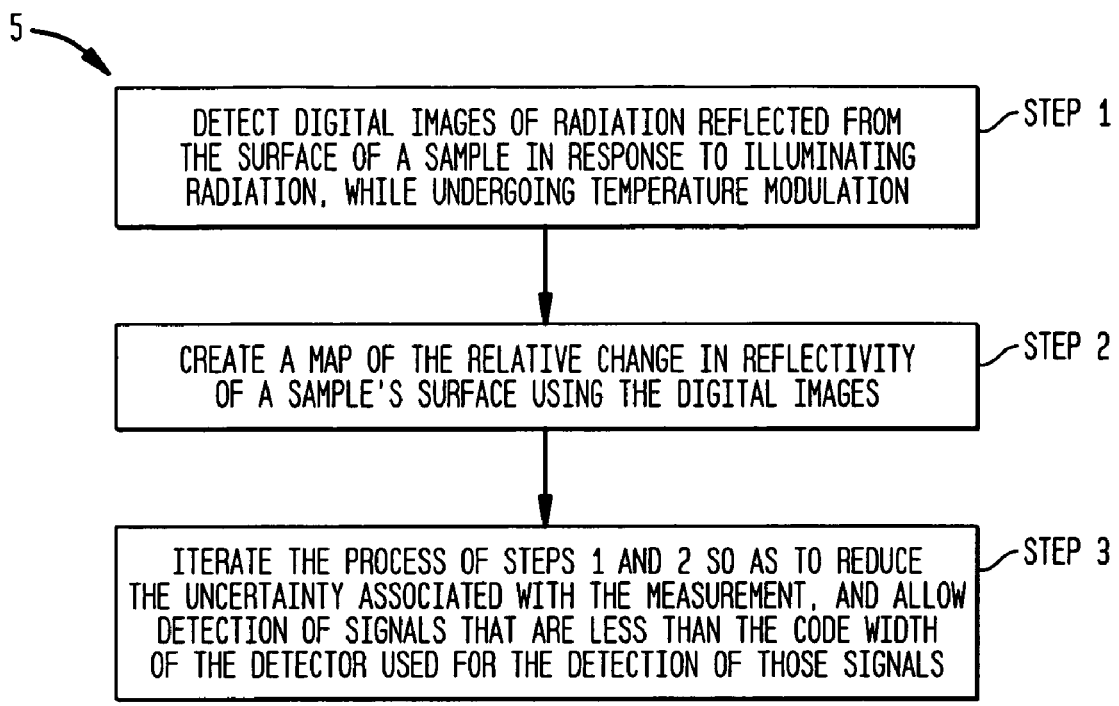
FIG. 1B shows a flow chart depicting various steps for acquiring thermoreflectance images according to some embodiments of the present invention.

The above equations can be evaluated for each individual pixel, thus generating 2-dimensional maps of both the signal magnitude and the phase. By way of example, FIG. 1B depicts a flow chart 5 illustrating various steps according to one embodiment of the invention for measuring thermoreflectance images. Step 1 involves acquiring digital images of radiation reflected from the surface of a sample in response to an illuminating radiation while a temperature modulation is applied to the sample. In step 2, a map of the reflectivity of a sample's surface is derived using the digital images captured in step 1 by the detector. In step 3, the above process of acquiring digital images is iterated a sufficient number of times so as to reduce the uncertainty associated with the measurement, and allow detection of signals that are less the code width of the detector used for detection of those signals.

In some embodiments, the noise in the CCD images can stem from signal independent thermal and readout noise, and from the signal-dependent shot noise. Because in many embodiments the signal is normalized for each pixel individually, the otherwise important photo-response non-uniformity noise (the most significant component of pattern noise) does not generally influence the noise in the ΔR/R image. Applicants have confirmed experimentally that the random uncertainty in ΔR/R can be expressed by the following relation:

$$\sigma_{\Delta R/R}(c, N) = \frac{\pi}{4} \sqrt{2 - \frac{\pi}{2}} \frac{1}{\sqrt{N}} \frac{1}{c} (\alpha\sqrt{c} + \beta) \quad (4)$$

where N is the number of iterations of a series of 4 images taken for each period of the temperature modulation, and c is the average CCD signal level (compare equation (1)) and α and β are variables describing the noise of the CCD camera, as discussed in more detail below. By way of example, Applicants measured α=0.207 and β=7.65 for a CCD camera utilized in some embodiments of this invention. With α and β defined as in Equation (4), the noise term 'd' used in equations (1-3) can be defined. The term 'd' is a random variable with a normalized Gaussian probability density, and so is fully specified by its mean and standard deviation. Its mean is zero (0) and its standard deviation is $$\sigma_d = \alpha\sqrt{c} + \beta.$$

While in some embodiments a homodyne detection system is utilized, in other embodiments a heterodyne detection system can be employed. For example, in a heterodyne detection, system the temperature of a sample under study can be modulated at one frequency ($f_1$) while the radiation illuminating the sample can be modulated at another frequency ($f_2$). The radiation reflected from the sample can then be detected at a difference (beat) frequency equal to the difference of said $f_1$ and $f_2$ frequencies, e.g., by utilizing a non linear device and a local oscillator. For example, in one embodiment the difference frequency can be about 20 Hz (e.g., by selecting $f_1$ to be 100 kHz and $f_2$ to be 100.02 kHz).

High Temperature Resolution

As discussed in more detail below, Applicants have discovered that the acquisition of images within each temperature modulation cycle can be iterated sufficient number of times (e.g., $10^6$ iterations) to allow detection of signals that are smaller than the digital detector's code width. For example, noise induced threshold crossing phenomenon (stochastic resonance), can be employed to enhance the detected signal-to-noise, using a sufficiently large number of iterations, and beyond a level that has been traditionally considered feasible. In some cases, the code width of the detector can be selected such that the combined signal and system noise is sufficiently large such that it can span across two or more adjacent quantization levels of the detector during at least part of the measurement period. Alternatively, in some embodiments of the present invention, white noise can be added to the signal to achieve the same result.

Figure 3A:
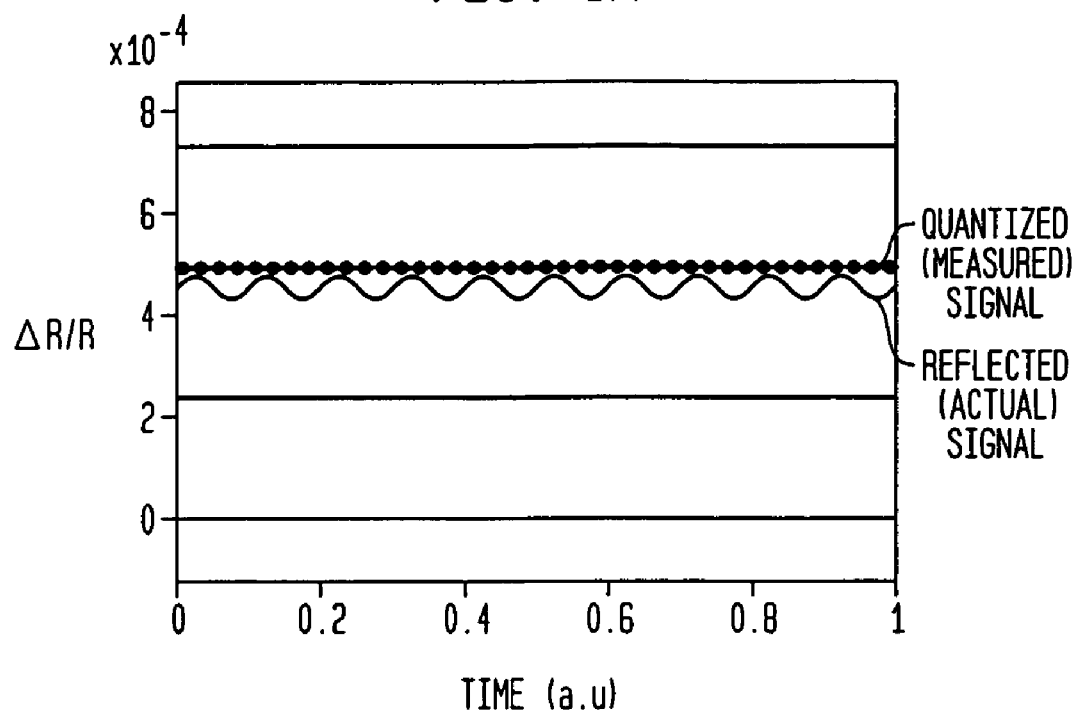
FIG. 3A is a schematic diagram depicting quantization of a detected thermoreflectance signal in the absence of added noise or when noise and/or signal levels are below quantization step.
Figure 3B:
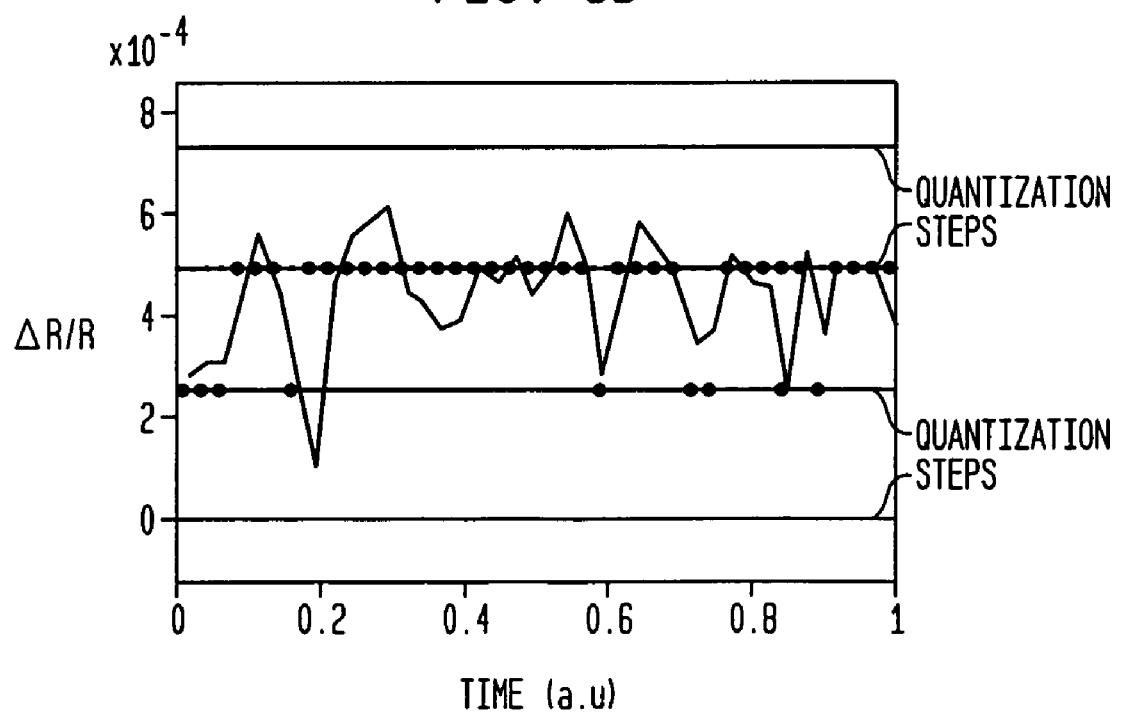
FIG. 3B is a schematic diagram depicting quantization of a detected thermoreflectance signal in the presence of added noise or when noise and/or signal levels allow the signal to cross between two or more adjacent quantization levels.

More particularly, as shown in FIG. 3A, in the absence of added noise, (or when noise and/or signal levels are insufficient) the smallest thermoreflected signal that can be detected may be limited by the size of the quantization step (i.e., the energy difference between two quantization steps) of the digital detector. For example, if the signal (e.g., detector pixel signal) oscillates near a particular quantization step without crossing between two adjacent quantization levels, its repeated averaging will not enhance detection (it will not enhance the signal-to-noise ratio) since overall magnitude of the signal is essentially constant due to being quantized to a single level. However, addition of noise (or choosing a detector with an appropriate quantization step) allows for the variation of a pixel signal between two or more adjacent quantization levels, as shown schematically in FIG. 3B. For example, in some embodiments, noise having a known characteristic (e.g., white noise or noise characterized by other known distributions) is added to the detection system so as to ensure that signal crossing between adjacent quantization levels occurs. Alternatively, the detector can be selected such that the noise inherently present in the detection process can cause such signal crossings. This can lead to a greater dynamic range of the measured signal, as signals between the quantization levels are also detected and averaged over a large number of iterations. This method of oversampling and averaging thus allows for the detection of signals below the code width of the detector used. This is particularly useful when the inherent or added noise can be substantially characterized as white noise, (i.e., noise which has a symmetric distribution about a zero mean, e.g., Gaussian noise). Thus, over sufficient number of iterations, the noise in the signal converges towards zero (or a constant offset), while the signal intensity is enhanced due to its periodic crossings of the signal between adjacent quantization levels.

Figure 6A:
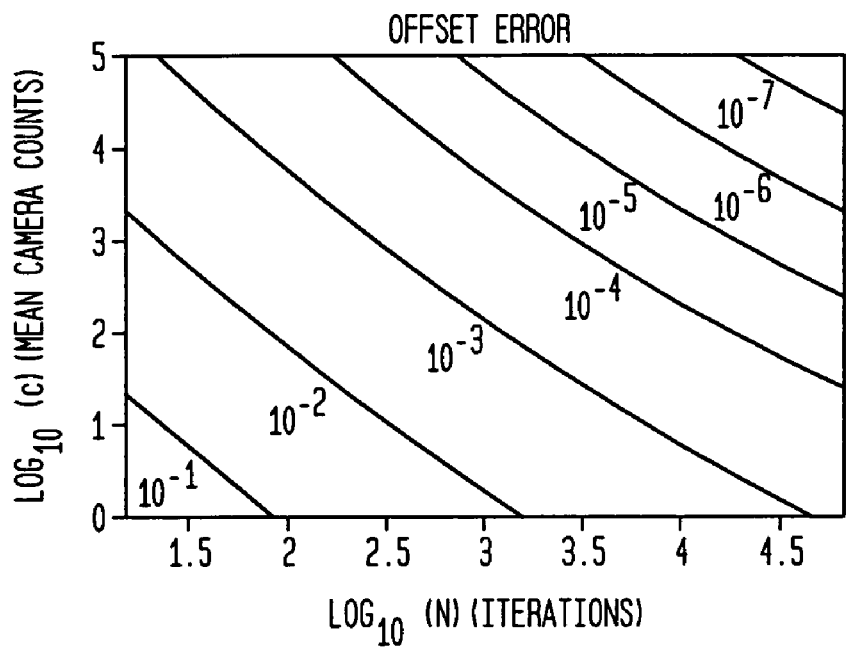
FIG. 6A is a plot of offset error in a thermoreflectance measurement ($\epsilon_{offset}$) as a function of number of iterations N and average CCD counts c.
Figure 6B:
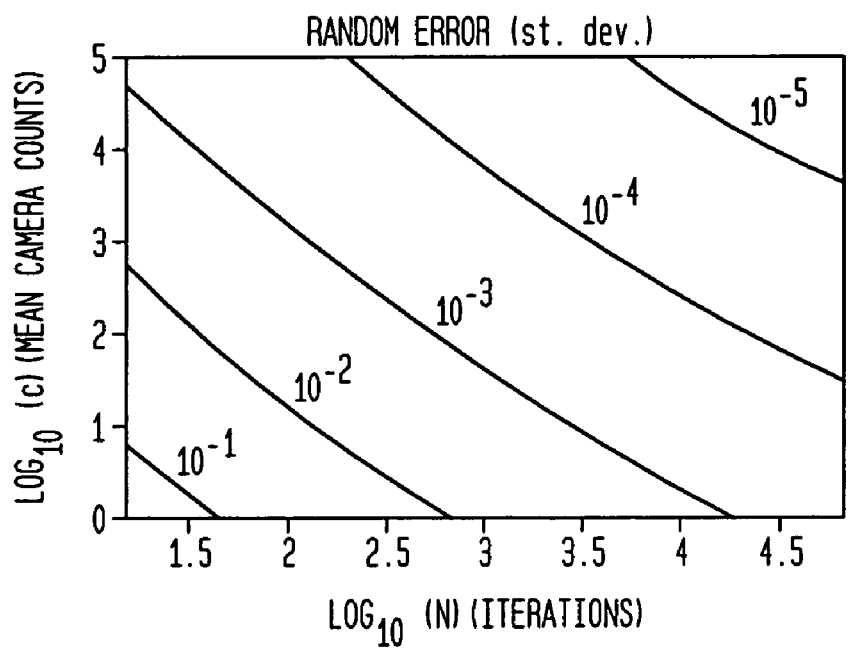
FIG. 6B is a plot of random error ($\epsilon_{random}$) in a thermoreflectance measurement as a function of number of iterations N and average CCD counts c.

The above Equation (4) relates the uncertainty in measurement of the thermoreflectance signal $$\left(\frac{\Delta R}{R}\right)$$

as a function of the number of iterations N and the average number of CCD counts c. FIGS. 6A and 6B show plots of the errors in $$\left(\frac{\Delta R}{R}\right),$$

as a function of iterations N and CCD counts c. FIG. (6A) corresponds to the error in the mean of the measured $$\left(\frac{\Delta R}{R}\right),$$

while FIG. (6B) corresponds to the random statistical error in the measured $$\left(\frac{\Delta R}{R}\right).$$

Together, they fully specify the error associated with $$\left(\frac{\Delta R}{R}\right).$$

While the plots are specifically calculated for the α and β of a particular CCD camera, they can easily be adapted for any other model once the coefficients α and β have been measured using Equations (20) and (21), introduced later. Nevertheless, the general features will remain the same. The plot indicates that the best experimental accuracy can be achieved by using a detector with a high bit depth and operating it close to saturation intensity, i.e., the uncertainty in the thermoreflectance signal $$\left(\frac{\Delta R}{R}\right)$$

decreases, as the average CCD counts and the number of iterations N increases.

For example, Applicants have recovered signals by employing a 12-bit CCD camera with a measured uncertainty that is smaller than the camera's code width. This is two orders of magnitude better than the standard results obtained using published techniques. This, in turn, can translate to an enhanced method of thermoreflectance measurements that can result in a temperature resolution in the range of about 1 mK to about 1K and more particularly in the range from about 1 mK to about 10 mK. In many embodiments, thermoreflectance measurements are performed by utilizing a digital detector having a high bit depth, (e.g., a detector with a bit depth in the range of 8 to 16). In other embodiments of the present invention, the detector may operate close to saturation intensity. As discussed in more detail in the examples below, above methods can be employed to perform thermoreflectance measurements of signals smaller than the code width of the digital detector used for these measurements Self-Contained Data Validation As noted above, in another aspect, the invention provides a method for determining the signal-to-noise ratio of a measurement from the measurement itself, or from the noise characteristics of the detection process.

Figure 4:
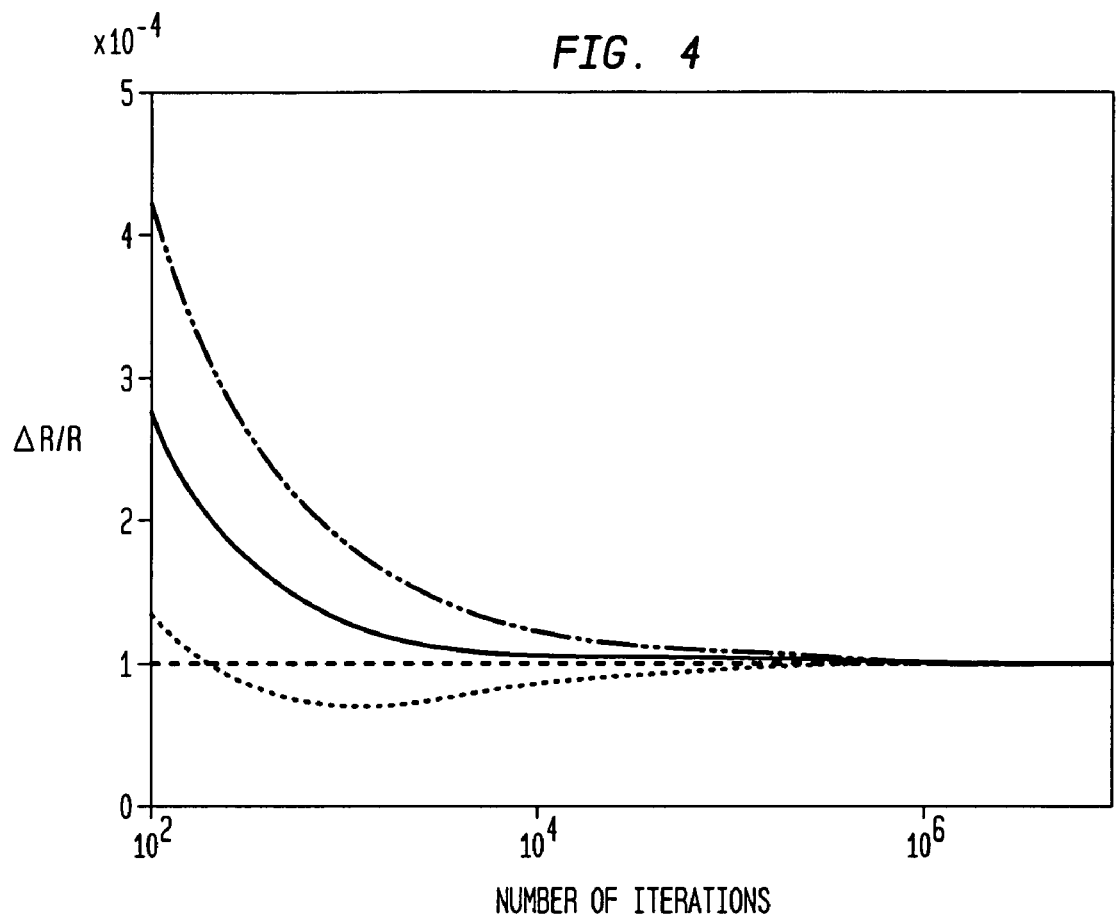
FIG. 4 is a plot depicting the change in uncertainty of a measured thermoreflectance signal as a function of number of iterations N.

By way of example, FIG. 4 shows that the signal uncertainty decreases as the number of iterations N increases. In FIG. 4, the dashed line represents ideal or desired thermoreflectance measurement, solid line depicts the expected value of the thermoreflectance, while the two dotted lines describe the plus/minus error associated with the measurement. Since the signal magnitude is not known a priori, it is important to know when enough iterations have been performed to achieve a particular temperature resolution, i.e. when the measurement has converged.

FIG. 4 shows one possible path: if an increase in the number of iterations does not change the signal magnitude, there have been enough iterations. However, this criterion can be cumbersome since (a) it requires several independent measurements, and (b) the measurement itself is not sufficient for its own validation. However, using the above Equation (3), it is possible to formulate a criterion that allows determination of the signal-to-noise ratio from the phase noise. The idea is that the phase of the signal does not vary much over small areas of the sample even if the signal changes significantly. This is true in the majority of cases with only a few exceptions such as (a) adjacent areas of heating and cooling, in which case there is an abrupt 180° phase shift, or (b) the case of thermal waves, where the phase changes gradually over the thermal wavelength. These are details that can be taken into account when setting up the criterion in a particular situation.

Figure 5:
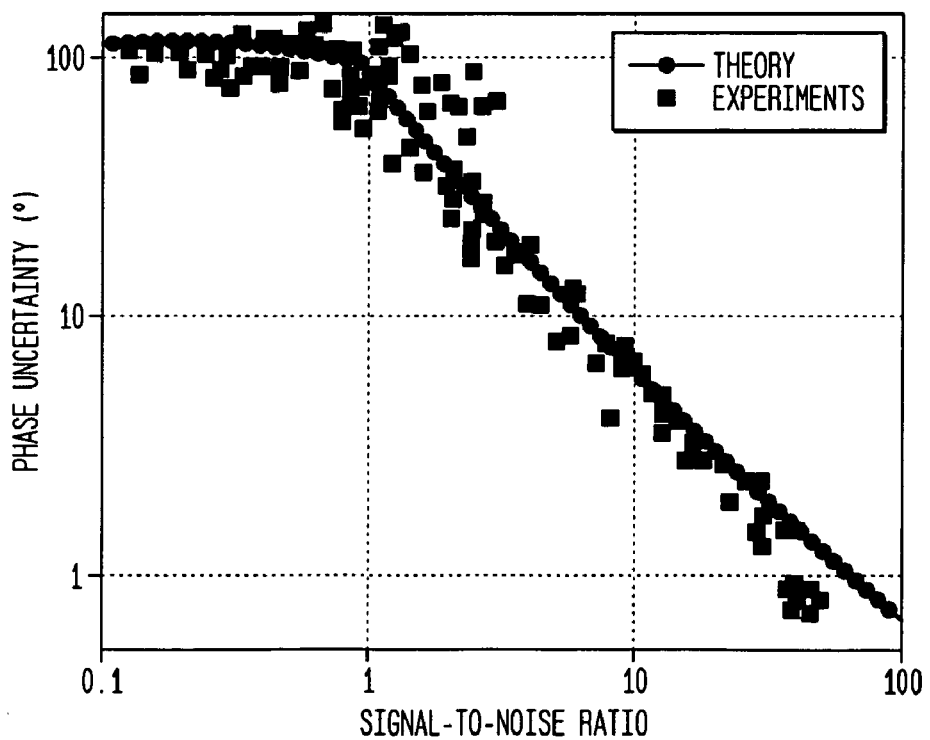
FIG. 5 shows that the uncertainty in the phase of a thermoreflectance measurement can be used to determine the signal-to-noise ratio according to one embodiment of the present invention.

FIG. 5 shows the phase uncertainty (determined from a 5 by 5 pixel area) as a function of the signal-to-noise ratio. FIG. 5 illustrates both a theoretical curve based on a numerical evaluation of Equation (3) for various phases, and experimental data from different samples. The number of iterations can be terminated when the phase uncertainty reaches a threshold (e.g., a pre-selected threshold). For example, the number of iterations can be terminated when the phase uncertainty reaches about 10 degrees. The threshold can be selected based on a particular application, and a desired signal-to-noise ratio.

FIG. 5 shows that theory and experiment agree very well, thus indicating the feasibility of utilizing the phase for estimating in tempore the signal-to-noise ratio. Its advantage compared to the traditional methods described above is that the measurement contains both the signal information and a quality control mechanism. This mechanism allows one to determine if large contrast in the ΔR/R image is due to statistical uncertainties, or instead represents meaningful data. For example, the relative stability of the phase values among a number of neighboring pixels can provide an indication of the signal-to-noise ratio.

In some embodiments of the invention, the noise characteristics of the detection process can be employed to predict an expected signal-to-noise ratio for the thermoreflectance signal as a function of the number of iterations as well as the number of detector counts corresponding to the non-modulating (dc) portion of the reflected signal. More specifically, in such embodiments, the error in the measurement can be derived by treating ΔR/R and φ as random variables with probability density functions (pdfs) that are seeded by the input noise in each pixel of the digital detector (herein referred to as the random variable d). A combination of shot noise and thermal read-out noise, both of which can be considered as Gaussian noise processes with a zero mean, contribute to the pixel signal noise. Accordingly, the pixel signal noise can be characterized by the following probability density function:

$$P_d = N(0, \sigma_d^2) \qquad (5)$$

where $N(\mu, \sigma^2)$ denotes a Gaussian pdf with a mean $\mu$ and variance $\sigma$. Without loss of generality, the noise $\sigma_d$ ad can be expressed in units of CCD counts, although fractional values of $\sigma_d$ are also considered, as the noise is modeled before the quantization step in the CCD camera. The standard deviation of the noise can then be expressed in units of CCD counts as:

$$\sigma_d = \alpha \sqrt{c} + \beta \qquad (6)$$

where variable $\alpha$ is selected to model the shot noise associated with the incoming photons (i.e., photons incident on the detector) and dark current, and variable $\beta$ models the noise components that do not depend on the incoming signal intensity (e.g., thermal noise).

During a signal measurement by the digital detector, the photo signal and the noise signal are quantized by the detector (e.g., by camera wells). This process is non-linear whose effect on the measurement generally depends nontrivially on the signal. However, if the noise in the incoming signal is larger than the quantization bin size of the digital detector (e.g., $\sigma_d > 1$), the effects of quantization noise can be represented as an additive (i.e., uncorrelated) white noise process with a standard deviation of $\sigma_{quant} = 1/\sqrt{12}$, as discussed in more detail below (Error Analysis). Hence, the effects of the quantization noise on the measurement output can be the same as that of the thermal noise, and can be absorbed in the $\beta$ coefficient in the above expression (Equation 6) of the pixel noise.

Each of the random variables $I_k$ in the above Equation (2) is constructed from the sum of N successive exposures of the digital detector (CCD camera) to incoming photons, and can be expressed by a Gaussian pdf ($P_{I_k}$) in accordance with the following relation:

$$P_{I_k} = N(\mu_k, N\sigma_d^2) \qquad (7)$$

where N denotes a Gaussian pdf with a mean ($\mu_k$) and standard deviation ($\sigma_d$). As the noise in each exposure is uncorrelated with the noise in the others, the noise variances for the N exposures add, thus resulting in the factor of N in the above equation. Further, the mean value ($\mu_k$) for the case in which each exposure corresponds to a full quarter-period of the temperature modulation can be expressed by the following relation:

$$\mu_k = N\left(c - \frac{4\Delta}{\pi\sqrt{2}}\left(\cos\left(\frac{\pi k}{2} - \frac{\pi}{4}\right)\sin(\Phi + \Psi) + \sin\left(\frac{\pi k}{2} - \frac{\pi}{4}\right)\cos(\Phi + \Psi)\right)\right) \qquad (8)$$

For cases in which the CCD camera acquires data for each exposure (image) for a period less than the full quarter-period of sample's temperature modulation, the expression in the above Equation (8) can be readily modified to take into account this temporal change in image acquisition—the difference in Equation (8), between the full quarter-period acquisition and the opposite extreme (delta ($\Delta$) function sampling) is only about 10%.

To calculate the probability distribution of the observed magnitude and phase of the thermoreflectance signal, the Gaussian pdf of Equation (6) can be propagated through Equations (3) and (4). In many embodiments of the invention, the magnitude of the constant background reflectance signal c is far larger than that of the noise (e.g., root mean square of the noise, $\sqrt{\sigma_d^2}$), and the amplitude of the modulated thermoreflectance signal. That is, $\mu_k \approx Nc >> \sqrt{N\sigma_d^2}$. Hence, the variance of $I_k$ in the denominator of Equation (3) can be ignored, and the above Equation (3) can be rewritten as:

$$\left|\frac{\Delta R}{R}\right| = \sqrt{\left[\frac{\pi}{\sqrt{2}}\frac{I_1 - I_3}{\sum_k \mu_k}\right]^2 + \left[\frac{\pi}{\sqrt{2}}\frac{I_2 - I_4}{\sum_k \mu_k}\right]^2} \quad (9)$$

$$= \sqrt{\left[\frac{\pi}{\sqrt{2}}\frac{I_1 - I_3}{4Nc}\right]^2 + \left[\frac{\pi}{\sqrt{2}}\frac{I_2 - I_4}{4Nc}\right]^2}$$

Since the $I_k$ variables (i.e., $I_1$, $I_2$, $I_3$ and $I_4$) are statistically independent random variables, the bracketed terms in the above equation are themselves random variables, thus allowing the following new independent random variables to be defined:

$$A = \frac{\pi}{\sqrt{2}}\frac{I_1 - I_3}{4Nc}, \quad P_A = N(\mu_A, \sigma^2) \quad (10)$$

$$B = \frac{\pi}{\sqrt{2}}\frac{I_2 - I_4}{4Nc}, \quad P_B = N(\mu_B, \sigma^2) \quad (11)$$

where $$\mu_A = \frac{\pi}{\sqrt{2}}\frac{\mu_1 - \mu_3}{4Nc} \quad (12)$$

$$\mu_B = \frac{\pi}{\sqrt{2}}\frac{\mu_2 - \mu_4}{4Nc} \quad (13)$$

$$\sigma^2 = \frac{\pi^2}{2}\frac{2N\sigma_d^2}{(4Nc)^2} = \frac{\pi^2}{16}\frac{\sigma_d^2}{Nc^2} \quad (14)$$

The thermoreflectance can then be defined as:

$$\left|\frac{\Delta R}{R}\right| = \sqrt{A^2 + B^2} \quad (15)$$

where A and B are random, independent and orthogonal vectors, and the thermoreflectance signal corresponds to the magnitude of A and B. The joint Gaussian pdf of A and B is given by the following relation:

$$P_{A,B}(A, B) = \frac{1}{2\pi\sigma^2}\exp\left(-\frac{(A - \mu_A)^2 + (B - \mu_B)^2}{2\sigma^2}\right) \quad (16)$$

By changing variables according to $A = r\cos\theta$ and $B = r\sin\theta$, the joint pdf of A and B in terms of the new variables can be obtained according to the following relation:

$$P_{r,\theta}(r, \theta) = \frac{r}{2\pi\sigma^2}\exp\left(-\frac{1}{2\sigma^2}[(r\cos\theta - \mu_A)^2 + (r\sin\theta - \mu_B)^2]\right) \quad (17)$$

By integrating the above equation (17) over the variable $\theta$, the joint pdf as a function of thermoreflectance "r" is given by the following relation:

$$P_r(r) = \frac{r}{\sigma^2}\exp\left(-\frac{r^2 + \mu_A^2 + \mu_B^2}{2\sigma^2}\right)I_0\left(r\frac{\sqrt{\mu_A^2 + \mu_B^2}}{\sigma^2}\right) \quad (18)$$

where $I_0$ denotes the $0^{th}$ order modified Bessel function. The first term in the above Equation (18), is the "Rician Distribution" and in the limit of low noise (small $\sigma$), the above equation collapses to a delta function distribution as shown in Equation (19). The above Equation (17) can also be integrated over the variable r to obtain a pdf for the variable $\theta$.

$$\left|\frac{\Delta R}{R}\right|_{ideal} = \sqrt{\mu_A^2 + \mu_B^2} = \frac{\Delta}{c} \quad (19)$$

The pdf in Equation (18) describes the statistics associated with the magnitude of the measured thermoreflectance signal. As such, it can be employed to theoretically determine the number of iterations (measurements) required to accurately measure a temperature difference so long as the average counts (c) of the detector and the characteristics of the input noise (e.g., the variables $\alpha$ and $\beta$ in the above Equation 6) are determined. The moments of the pdf in the above Equation 19 are given by the following relations:

$$E\left[\frac{\Delta R}{R}\right] = \sqrt{2}\,\sigma\exp\left(-\frac{\mu_A^2 + \mu_B^2}{2\sigma^2}\right) \quad (20)$$

$$\left[\frac{1}{2}\sqrt{\pi}\left(1 + \frac{1}{2}\frac{\mu_A^2 + \mu_B^2}{\sigma^2}\right)\exp\left(\frac{\mu_A^2 + \mu_B^2}{4\sigma^2}\right)I_0\left(\frac{\mu_A^2 + \mu_B^2}{4\sigma^2}\right) + \frac{\sqrt{\pi}}{4\sigma^2}\frac{\mu_A^2 + \mu_B^2}{4\sigma^2}\exp\left(\frac{\mu_A^2 + \mu_B^2}{4\sigma^2}\right)I_1\left(\frac{\mu_A^2 + \mu_B^2}{4\sigma^2}\right)\right]$$

$$E\left[\left(\frac{\Delta R}{R}\right)^2\right] = 2\sigma^2 + \mu_A^2 + \mu_B^2 \quad (21)$$

More specifically, the error in a thermoreflectance measurement can be well approximated by the sum of two errors $\epsilon_{offset}$ and $\epsilon_{random}$. $\epsilon_{offset}$ can be represented by the difference between the first moment of the pdf in the above Equation (18) and an ideal signal as given in the above Equation (19). That is, $\epsilon_{offset}$ can be obtained in accordance with the following relation:

$$\varepsilon_{offset} \equiv E\left[\frac{\Delta R}{R}\right] - \frac{\Delta R}{R}\bigg|_{ideal} = E\left[\frac{\Delta R}{R}\right] - \sqrt{\mu_A^2 + \mu_B^2} \quad (22)$$

The random error ($\epsilon_{random}$) is defined by the standard deviation of the pdf in the above Equation (21), and is indicative of the random measurement error. $\epsilon_{random}$ can be obtained in accordance with the following relation:

$$\varepsilon_{random} \equiv \sqrt{E\left[\left(\frac{\Delta R}{R}\right)^2\right] - E\left[\frac{\Delta R}{R}\right]^2} \quad (23)$$

If no thermoreflectance signal is present (i.e., if $\mu_A^2 + \mu_B^2 = 0$), the above equation for $\epsilon_{random}$ can be can be expressed in terms of the fundamental noise $\sigma_d$ of a CCD pixel:

$$\varepsilon_{random}\big|_{\mu_A^2 + \mu_B^2 = 0} = \left(\sqrt{2 - \frac{\pi}{2}}\right)\sigma \quad (24)$$

$$= \left(\sqrt{2 - \frac{\pi}{2}}\right) \frac{\pi}{4} \frac{\sigma_d}{c\sqrt{N}}$$

$$= \left(\sqrt{2 - \frac{\pi}{2}}\right) \frac{\pi}{4} \frac{(\alpha\sqrt{c} + \beta)}{c\sqrt{N}}$$

In some embodiments, by measuring $$\frac{\Delta R}{R}$$

with no thermoreflectance signal for a variety of count levels c and iterations N, the $$\varepsilon_{random}|_{\mu_A^2 + \mu_B^2 = 0}$$

can be measured to determine the input noise ($\sigma_d$), as well as variables $\alpha$ and $\beta$. Once these variables are known for a specific digital detector (CCD camera), the accuracy of thermoreflectance measurements obtained by utilizing that detector can be analytically predicted as a function of c and N. Alternatively, the noise parameters $\alpha$ and $\beta$ can be determined directly by measuring the pixel noise in normal images (images for which a thermoreflectance signal is present) as a function of N and c.

By way of example, FIGS. 6A and 6B depict plots of $\epsilon_{offset}$ and $\epsilon_{error}$ as a function of number of measurement iterations N and number of counts c for a CCD camera characterized by noise input variables $\alpha=0.207$ and $\beta=7.650$ and a thermoreflectance signal magnitude of $$\frac{\Delta R}{R} = 10^{-4}.$$

For a given level of dc camera signal c, this chart can be employed to determine the number of iterations N required to achieve a given measurement accuracy.

The above exemplary embodiments present at least two significant improvements for CCD based thermoreflectance microscopes. One of the improvements enables the measurement of temperature maps with a henceforth unsurpassed combination of high temperature resolution, good spatial resolution, and large field of view. For example, in many embodiments, a spatial resolution in a range of about 200 nm to about 1 μm (micron), and preferably in a range of about 200 nm to about 500 nm, and a temperature resolution in a range of about 1 mK to about 1K, and preferably in a range of about 1 mK to about 10 mK can be achieved. The other improvement allows the user to determine the reliability of the acquired data without recourse to either additional measurements using the same technique or an independent one. The measurements thus have a self-contained quality control feature. Because of these features, the above thermoreflectance technique of the invention enables new applications that were previously unattainable.

To further illustrate various aspects of the invention, the following examples are provided. It should be understood that these examples are provided only for illustration purposes and do not necessarily represent optimal results that can be obtained by employing the teachings of the invention.

EXAMPLE 1

Figure 7:
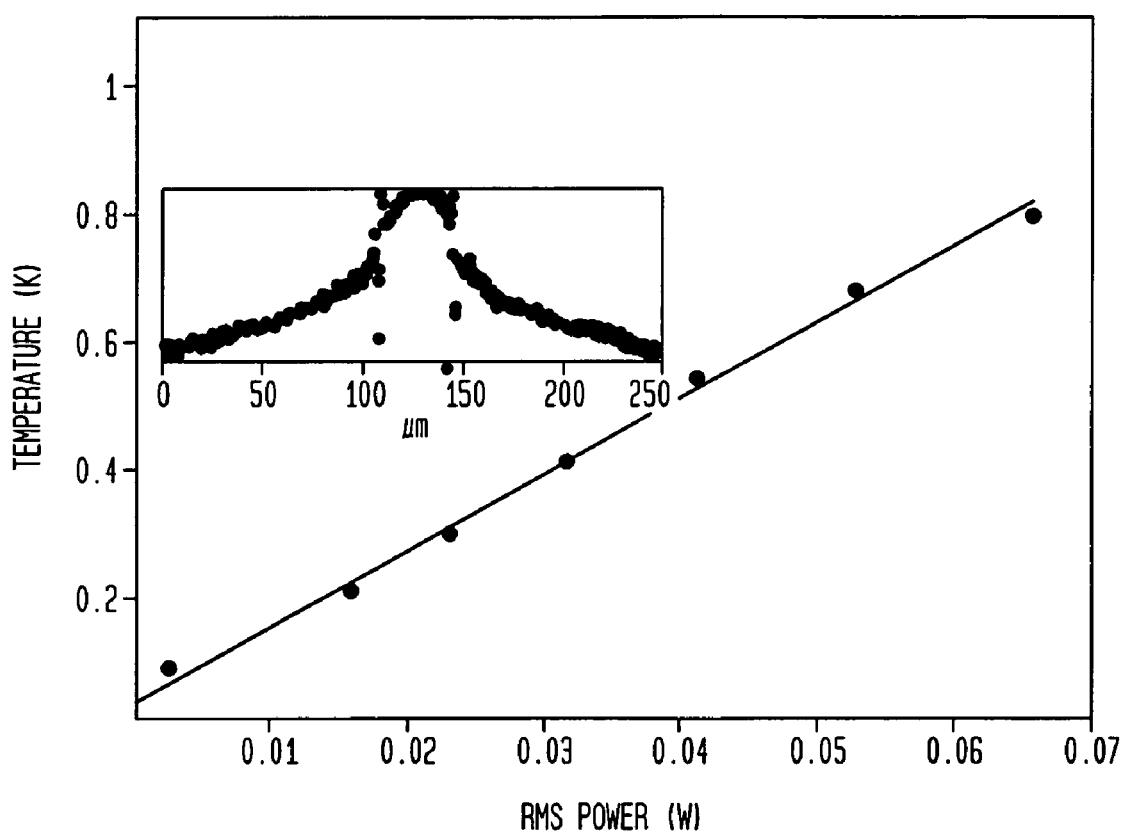
FIG. 7 shows thermoreflectance profile of a boron diffused silicon resistor illustrating that signal values below the code width (equal to about 2.93 K in this example) of a digital detector can be measured in accordance with an embodiment of the present invention.

To show the efficacy of the methods of the invention in measuring thermoreflectance signals having magnitudes smaller than the least significant bit of a digital detector utilized for detecting those signals, the linear temperature dependence of a boron-doped Si resistor with Ohmic heating power was measured, as shown in FIG. 7. A current applied to the resistor was modulated sinusoidally at a frequency of 6 Hz, resulting in a modulated temperature (and reflectance signal) at 12 Hz due to Joule heating. The trigger of the CCD camera was locked to the reflectance signal at 48 Hz. The doped resistor's thermoreflectance coefficient ($\kappa=2.20\times10^{-4}$) was measured by using a microthermocouple, as a reference temperature monitor. The mean level of camera counts for the measurements was 1550, giving rise to a quantization limit temperature level of 2.93 K. The data presented in FIG. 7 shows the linear dependence of the measured temperature on the applied electrical power, even though the signals are measured far below a temperature corresponding to the quantization limit of the camera. For most of these measurements, $N=10^5$ iterations were used, resulting in a measurement time of about 2.3 hours. The standard deviation of the error was about 18 mK.

EXAMPLE 2

Figure 8A:
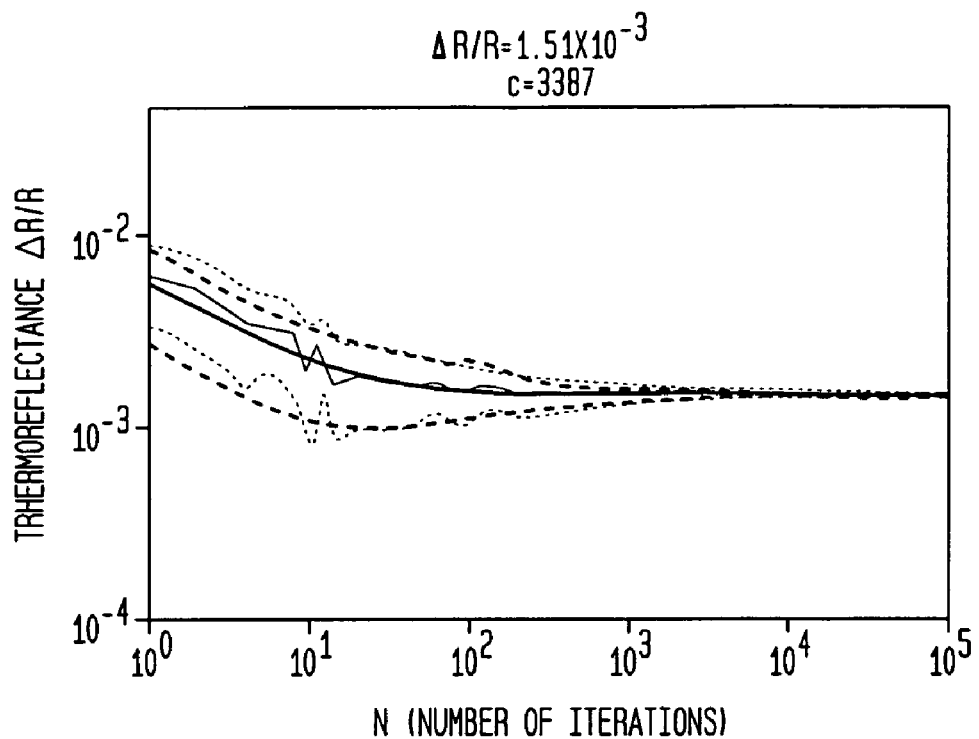
FIG. 8A depicts the behavior of a thermoreflectance signal as a function of number of iterations N, for a relatively large signal.
Figure 8B:
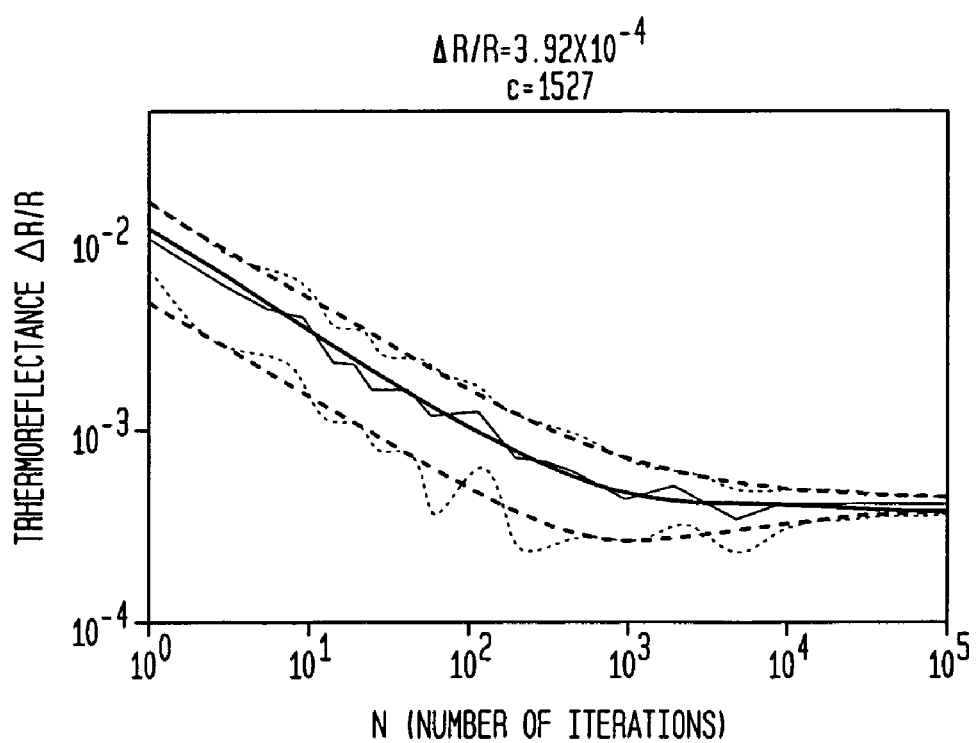
FIG. 8B depicts the behavior of a thermoreflectance signal as a function of number of iterations N, for a relatively smaller signal.

To provide experimental evidence for the above method of theoretically calculating the signal-to-noise ratio of a thermoreflectance measurement by utilizing the pre-determined noise characteristics of the measurement process, a 25 pixel (5×5) area of uniform temperature excitation was imaged by varying numbers of iterations. Two independent levels of illumination and excitation were employed. Separate measurements, together with the use of the above Equation (24), resulted in the following noise parameters: $\alpha=0.207$ and $\beta=7.650$. FIGS. 8A and 8B provide graphs depicting two examples of the behavior of thermoreflectance measurements as the number of measured iterations (N) is increased: one of the larger thermoreflectance signal and the other for the smaller thermoreflectance signal. The grey dotted lines depicts the mean measured thermoreflectance of the 25 pixels (from Equation (20)), the black solid line depicts the theoretically expected thermoreflectance, and the dotted lines denote the theoretical $\pm 1-\sigma$ error bars of the measurements (from Equation (21)). This data illustrates that only for sufficiently large number of iterations N, the mean of the measurements converge. If the averaging is insufficient (small N), the Gaussian pixel noise can give rise to a large systematic offset error in the measured thermoreflectance.

EXAMPLE 3

To provide further experimental evidence that the methods of the invention allow enhanced temperature resolution with smaller uncertainty of the measurement the following example can be considered. A gold surface (typical contact material of an electronic circuit) was illuminated using light of wavelength 467 nm, a wavelength at which the thermoreflectance coefficient of gold is particularly high, $\kappa=3.3\cdot10^{-4}K^{-1}$. Using this number, the temperature resolution can be calculated as $\Delta T=\kappa^{-1} \Delta R/R$. This means that, for a 12 bit camera operated close to saturation, instead of being able to resolve temperature changes with an uncertainty of 1K per pixel, the use of the improved method in this example permits measuring thermoreflectance signals with uncertainties smaller than 10 mK per pixel.

Error Analysis

Figure 9:
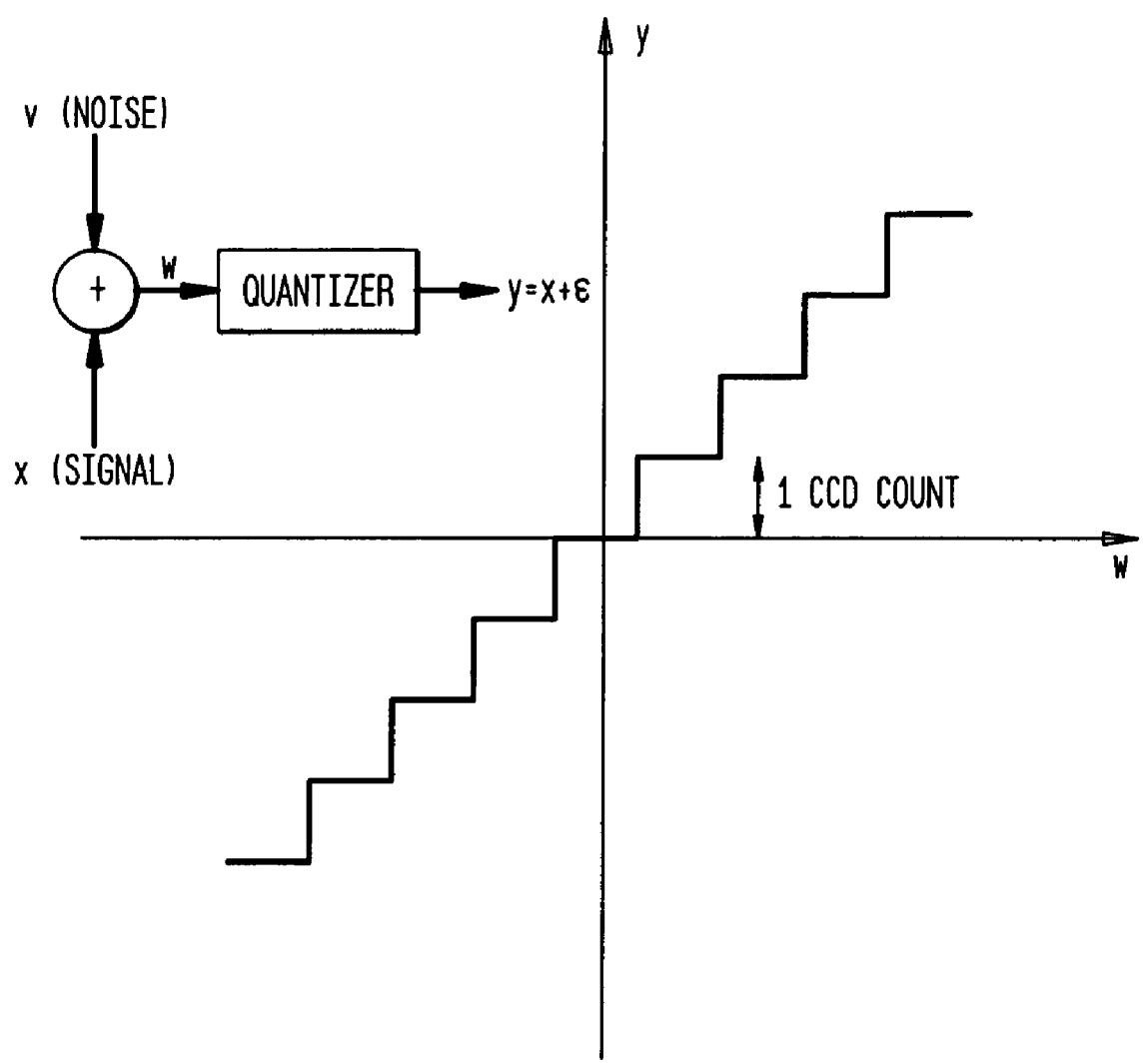
FIG. 9 is a schematic view of the quantization process utilized in some embodiments of the present invention.

As mentioned earlier, quantization is an inherently nonlinear process. The signal flow diagram and transfer function for the process are shown in FIG. 9. A signal to be measured (x) is combined with some additive noise (v), and the resultant signal (w) is put through a quantizer. The quantizer output (y) is related to the original signal by an error term ($\epsilon$), which has error due to the additive noise and the quantization process.

For what follows it is assumed that the noise signal (v) is Gaussian, white, and has a standard deviation of $\sigma_d$. In other words v=d, from the discussion of thermoreflectance.

It is not generally appropriate to treat the error $\epsilon$ like a simple independent noise source similar to v. Unfortunately, the error $\epsilon$ is not independent of the signal x. In fact, if w is so small that it never crosses into any adjacent quantization levels, the signal and error are exactly negatively correlated ($\epsilon$=-x). In such a situation, assuming that $\epsilon$ could be modeled as a zero mean Gaussian noise source would be wrong. However, if the standard deviation of v is much greater than the quantization bin size, the statistics of $\epsilon$ begin to approach those of v. A quantitative estimate of when this change occurs can be made by calculating the correlation of x and $\epsilon$, given by E[x $\epsilon$], where E denotes the expectation value.

From FIG. 9, the expression for the pdf of $\epsilon$ conditioned on a known value of the signal is given by:

$$P_{\epsilon|x} = \sum_{k=-\infty}^{\infty} \delta(\epsilon + x - k) \int_{-1/2+k}^{1/2+k} P_v(w - x) dw \quad (A1.1)$$

Here $P_v$ denotes the pdf of the noise v. The probability distribution takes the form of a sum of delta functions at discrete values of k, corresponding to each of the output quantization levels of the A-to-D converter. The number of quantization levels is assumed infinite so that each bin can be presumed identical. This assumption holds as long as the signal does not clip (i.e., clear of the maximum and minimum quantization levels). The integral in above equation (A1.1) calculates the weight (likelihood) of each possible output quantization bin according to the probability that the sum of the input and noise falls in the range corresponding to that bin. For Gaussian input noise, the integrals can be analytically expressed in terms of the error function.

Substituting in the Gaussian pdf and integrating above equation, the following relation is obtained:

$$P_{\epsilon|x} = \frac{1}{2} \sum_{k=-\infty}^{\infty} \delta(\epsilon + x - k) \quad (A.1.2)$$
$$\left\{ \text{erf}\left( \frac{1}{\sigma_d \sqrt{2}} \left[ \frac{1}{2} + k - x \right] \right) - \text{erf}\left( \frac{1}{\sigma_d \sqrt{2}} \left[ -\frac{1}{2} + k - x \right] \right) \right\}$$

Here erf denotes the error function.

The above equation A.1.2, allows the correlation between $\epsilon$ and x to be determined as follows $$E[x\epsilon] = \int_{-\infty}^{\infty} x\epsilon (P_{\epsilon|x}) d\epsilon \quad (A.1.3)$$

Equation A.1.3 can be used to write the result in terms of a sum over all the quantization levels as indicated below:

$$E[x\epsilon] = \frac{x}{2} \sum_{k=-\infty}^{\infty} (k - x) \quad (A.1.4)$$
$$\left\{ \text{erf}\left( \frac{1}{\sigma_d \sqrt{2}} \left[ \frac{1}{2} + k - x \right] \right) - \text{erf}\left( \frac{1}{\sigma_d \sqrt{2}} \left[ -\frac{1}{2} + k - x \right] \right) \right\}$$

Figure 10:
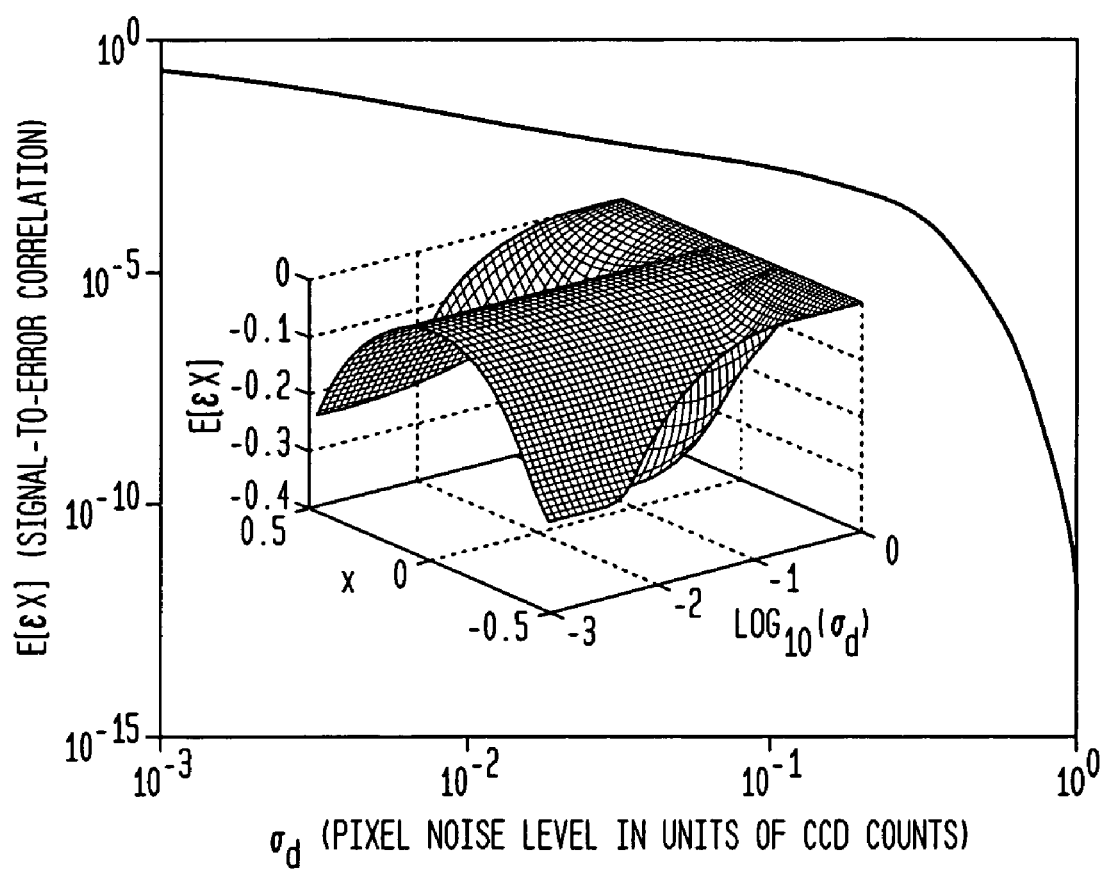
FIG. 10 shows a plot depicting the relation between pixel noise level and a correlation between quantization error and input signal.

This sum can be explicitly computed and the results are shown in FIG. 10. As shown in FIG. 10, there is a negative correlation between E[x$\epsilon$] and signal pixel noise level ($\sigma$d). The result of this analysis is that the noise levels on the order of the quantization bin size or larger, the correlation between error and the input becomes very small, justifying the treatment of $\epsilon$ as an independent noise source. Above this threshold, the variance is well approximated by the standard formula for quantization noise:

$$\sigma_\epsilon^2 = E[\epsilon^2] - E[\epsilon]^2 \cong \sigma_\epsilon^2 + \frac{1}{12} \quad (A.1.5)$$

This can be confirmed by plotting the first and second moments of $\epsilon$ using summations similar to equation A.1.4.

$$E[\epsilon] = \frac{1}{2} \sum_{k=-\infty}^{\infty} (k - x) \left\{ \text{erf}\left( \frac{1}{\sigma_d \sqrt{2}} \left[ \frac{1}{2} + k - x \right] \right) - \text{erf}\left( \frac{1}{\sigma_d \sqrt{2}} \left[ -\frac{1}{2} + k - x \right] \right) \right\} \quad (A.1.6)$$
$$= 0$$

$$E[\epsilon^2] = \frac{1}{2} \sum_{k=-\infty}^{\infty} (k - x)^2 \left\{ \text{erf}\left( \frac{1}{\sigma_d \sqrt{2}} \left[ \frac{1}{2} + k - x \right] \right) - \text{erf}\left( \frac{1}{\sigma_d \sqrt{2}} \left[ -\frac{1}{2} + k - x \right] \right) \right\} \quad (A.1.7)$$

Figure 11:
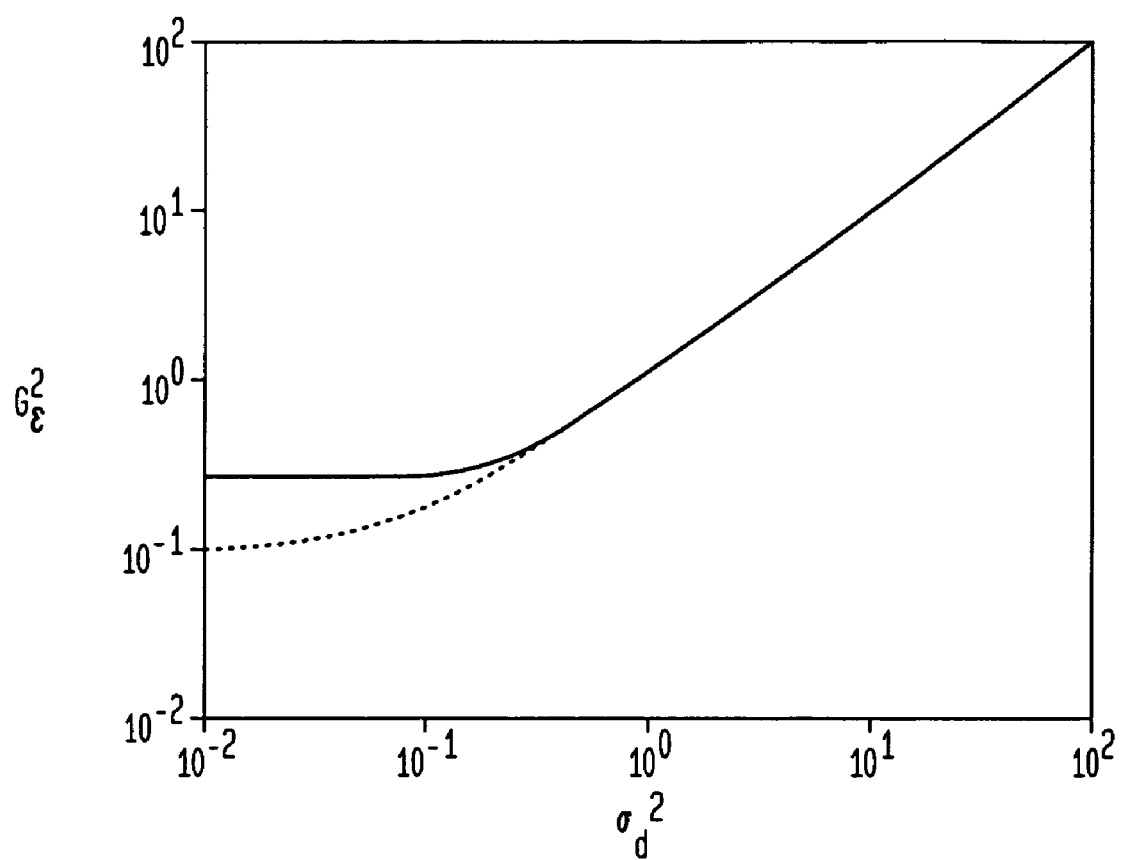
FIG. 11 is a plot showing the relation between the quantization error and variance associated with input noise.

The true noise variance $\sigma_\epsilon^2$ is shown in FIG. 11 and compared to the standard approximation of equation A.1.5. The formula is very accurate for input noise signals greater than around half the quantization bin size.

Those having ordinary skill in the art will also appreciate that various modifications can be made to the above embodiments without departing from the scope of the invention. For example, it should also be understood that the above teachings of the invention can also be applied to other modulation imaging techniques, such as electroreflectance (the electric field in the sample is varied) and piezoreflectance (a time varying pressure is applied to the sample). Further, the teachings of the invention are not limited to CCD detectors, but can be practiced with other digital imaging systems, such as CMOS imaging detectors.

The invention claimed is:

1. A method of performing thermoreflectance measurements, comprising:
acquiring digital images of radiation reflected from a surface of a sample in response to an illuminating radiation while a temperature modulation is applied to the sample,
deriving a map of relative change in reflectivity of said sample surface based on said images, and
repeating acquisition of digital images until uncertainty in the reflectivity change is reduced to a value such that relative changes in the reflectivity signals detected are less than a code width of said imaging system.

2. The method of claim 1, further comprising selecting the number of acquired images to be greater than about $10^3$.

3. The method of claim 1, further comprising selecting the number of acquired images to be greater than about $10^4$.

4. The method of claim 1, further comprising selecting the number of acquired images to be greater than about $10^5$.

5. The method of claim 1, further comprising selecting the number of acquired images to be greater than about $10^8$.

6. The method of claim 1, further comprising selecting the number of acquired images to be in a range of about $4\times10^3$ to about $8\times10^8$.

7. The method of claim 1, wherein the step of acquiring digital images further comprises utilizing a digital lock-in technique.

8. The method of claim 7, wherein said digital lock-in technique comprise the four-bucket lock-in method.

9. A method of performing thermoreflectance measurements, comprising:
modulating temperature of a sample at a selected modulation frequency (f),
illuminating a portion of the sample with radiation having one or more selected wavelength components,
utilizing a digital imaging system having a plurality of pixels to detect radiation reflected from the sample in response to said illumination to generate reflectance images of the sample, wherein said imaging system is triggered to obtain a selected number of reflectance images in one period of the temperature modulation,
calculating from said images a map of relative reflectance changes of said sample, and
iterating said step of acquiring reflectance images over a sufficient number of periods of said temperature modulation so as to obtain a sufficiently small uncertainty in the calculated relative reflectance such that signals smaller than a code width of said digital imaging system can be detected.

10. The method of claim 9, wherein the uncertainty in the calculated relative reflectance change is less than about $10^{-5}$ per pixel.

11. The method of claim 9, wherein the uncertainty in the calculated relative reflectance change is less than about $10^{-6}$ per pixel.

12. The method of claim 9, wherein the uncertainty in the calculated relative reflectance change is less than about $10^{-7}$ per pixel.

13. The method of claim 9, further comprising averaging signals detected by a plurality of neighboring pixels so as to reduce the uncertainty in the calculated relative reflectance change.

14. The method of claim 9, further comprising obtaining four reflectance images within each period of the temperature modulation.

15. The method of claim 14, further comprising summing respective images in a plurality of modulation periods to obtain a signal $I_k$, in accordance with the relation $$I_k(x,y) \equiv \sum_{i=1}^{N} \left[ \left( \frac{4}{T} \int_{(4i+k)\frac{T}{4}}^{(4i+k+1)\frac{T}{4}} [c(x,y) + \Delta(x,y)\cos(\omega t + \Phi(x,y) + \Psi)] dt \right) + d(x,y) \right]$$

$$k \in \{1, 2, 3, 4\}$$

wherein:
c represents the time independent component of the signal,
$\Delta$ is the amplitude of the modulated component of the signal,
d is the noise present prior to quantization,
$\Delta R/R$ is the intensity of the thermoreflectance signal,
$\phi$ represents the phase of the temperature modulation,
N is the number of iterations,
$\omega$ is frequency of modulation,
T is the period of modulation, and
$\Psi$ is an arbitrary uniform phase offset.

16. The method of claim 9, wherein said iterating step is performed over at least about $10^3$ periods of said temperature modulation.

17. The method of claim 9, wherein said iterating step is performed over at least about $10^6$ periods of said temperature modulation.

18. The method of claim 9, further comprising calculating a relative temperature modulation map of said sample based on said relative reflectance map.

19. The method of claim 18, wherein said temperature modulation map exhibits a temperature resolution in a range of about 1 mK to about 1 Kelvin.

20. The method of claim 18, wherein said temperature modulation map exhibits a temperature resolution in range of about 1 mK to about 10 mK.

21. The method of claim 18, wherein said temperature modulation map exhibits a spatial resolution of a few hundred nanometers.

22. The method of claim 18, wherein said temperature modulation map exhibits a spatial resolution in a range of about 200 nanometers to about 1 micron.

23. The method of claim 18, wherein said temperature modulation map exhibits a spatial resolution in a range of about 200 nm to about 500 nm.

24. The method of claim 18, wherein said temperature modulation map exhibits a spatial resolution in a range of about 200 nm to about 300 nm.

25. The method of claim 9, wherein said digital imaging system comprises a CCD camera.

26. A method of digitally detecting a modulated radiation signal, comprising:
for each of a plurality of modulation periods of said signal, triggering a digital detector at a plurality of time intervals to generate a plurality of read-out signals in response to detection of said modulated signal, generating a plurality of average output signals each corresponding to an average of read-out signals obtained at respective time intervals in said modulation periods, deriving a magnitude of said modulated signal based on said average output signals, wherein a number of said read-out signals is selected to be sufficiently large such that an uncertainty in said derived modulated signal is less than a code width of said detector.

27. The method of claim 26, wherein said signal corresponds to thermoreflectance of a substance.

28. The method of claim 26, wherein said signal corresponds to electroreflectance of a substance.

29. The method of claim 26, wherein said signal corresponds to piezoreflectance of a substance.

30. The method of claim 26, wherein said signal corresponds to photoreflectance of a substance.

31. A method of performing thermoreflectance measurements, comprising adding noise having a known distribution about an average value to a digital detection system such that a root-mean-square of the noise is greater than a spacing between quantization levels of said detection system, utilizing said detection system to acquire digital images of radiation reflected from a surface of a sample in response to an illuminating radiation while a temperature modulation is applied to the sample, deriving a map of relative changes in reflectivity of said sample surface based on said images, and repeating acquisition of digital images until uncertainty in the reflectivity changes is reduced to a value less than said spacing between the quantization levels.

32. A method of performing thermoreflectance measurements, comprising:

modulating temperature of sample at a selected modulation frequency $f_1$, illuminating a portion of the sample with radiation modulated at a different frequency $f_2$, utilizing a digital imaging system to detect radiation reflected from the sample, modulated at a difference frequency equal to a difference of said $f_1$ and $f_2$ frequencies in response to said illumination to generate reflectance images of the sample, wherein said imaging system is triggered to obtain a selected number of reflectance images in one cycle of the oscillation of said intermediate frequency, calculating from said images a map of relative reflectance changes of said sample, iterating said step of acquiring reflectance images of a sufficient number of oscillation cycles at said difference frequency, so as to obtain a sufficiently small uncertainty in the calculated relative reflectance change such that signals smaller than the code width of said digital imaging system can be detected.

* * * * *